United States Patent
Yokozeki et al.

(10) Patent No.: US 7,056,291 B2
(45) Date of Patent: Jun. 6, 2006

(54) ARTERIOSCLEROSIS EVALUATING APPARATUS

(75) Inventors: Akihiro Yokozeki, Komaki (JP); Yoshihisa Miwa, Komaki (JP)

(73) Assignee: Colin Medical Technology Corp., Komaki (JP)

( * ) Notice: Subject to any disclaimer, the term of this patent is extended or adjusted under 35 U.S.C. 154(b) by 292 days.

(21) Appl. No.: 10/760,703

(22) Filed: Jan. 21, 2004

(65) Prior Publication Data
US 2004/0220481 A1 Nov. 4, 2004

(30) Foreign Application Priority Data
Jan. 24, 2003 (JP) .............................. 2003-015815

(51) Int. Cl.
*A61B 5/00* (2006.01)

(52) U.S. Cl. ...................... 600/485; 600/485; 600/490; 600/494

(58) Field of Classification Search ...................... None
See application file for complete search history.

(56) References Cited

U.S. PATENT DOCUMENTS
5,711,303 A * 1/1998 Shimizu et al. ............. 600/490

FOREIGN PATENT DOCUMENTS
JP     A 2001-190506     7/2001

* cited by examiner

*Primary Examiner*—Robert Nasser
*Assistant Examiner*—Karen E. Toth
(74) *Attorney, Agent, or Firm*—Oliff & Berridge, PLC

(57) ABSTRACT

An arteriosclerosis evaluating apparatus 10 includes an arteriosclerosis evaluating procedure 46 (Steps S7, S8, S9, and S10) that evaluates arteriosclerosis of a living subject, based on a relationship between difference ΔP of internal and external pressure of an artery of the subject in the state in which the pressure difference ΔP is in equilibrium, and amplitude AM of a pulse wave produced from the artery. Therefore, the present apparatus 10 can as easily as possible evaluate the arteriosclerosis of the subject based on a characteristic curve 58 representing the relationship between in-equilibrium pressure difference ΔP and pulse-wave amplitude AM which curve is obtained from a pressing pressure Pc of a cuff 12 wound around a certain portion of the subject, and the pulse wave produced from the artery.

13 Claims, 10 Drawing Sheets

ARTERIOSCLEROSIS EVALUATING APPARATUS

BACKGROUND OF THE INVENTION

1. Field of the Invention

The present invention relates to an arteriosclerosis evaluating apparatus that evaluates arteriosclerosis of a living subject, based on a characteristic of subject's artery in a state in which difference of internal and external pressure of the artery is in equilibrium.

2. Related Art Statement

Evaluation of arteriosclerosis is frequently done for the purpose of, e.g., preventing adult disease such as cerebral hemorrhage or ischemic heart disease, and improvements of the evaluation technique are needed. There is known an arteriosclerosis evaluating apparatus that uses pulse-wave propagation velocity as an index for evaluating arteriosclerosis. This arteriosclerosis evaluating apparatus is disclosed by, e.g., Japanese Patent Publication No. 2001-190506. The disclosed arteriosclerosis evaluating apparatus includes a blood pressure measuring means for measuring a diastolic blood pressure of a living subject; a normal pulse-wave propagation velocity calculating means for calculating, on an assumption that the subject is normal, a normal pulse-wave propagation velocity of the subject, based on an actual age of the subject and the measured diastolic blood pressure of the subject, according to a predetermined formula; an actual pulse-wave propagation velocity calculating means for calculating an actual pulse-wave propagation velocity of the subject, based on an actual pulse wave detected from the subject; and an index calculating means for calculating, as an index of arteriosclerosis, a difference of the actual and normal pulse-wave propagation velocities. As arteriosclerosis of a living subject advances, an actual pulse-wave propagation velocity of the subject deviates from a normal pulse-wave propagation velocity of the same. Thus, the arteriosclerosis of the subject can be easily evaluated.

The above-indicated arteriosclerosis evaluating apparatus that uses the pulse-wave propagation velocity as the evaluation index has been so simplified in construction and so lowered in price, owing to the technical developments, that the apparatus can be actually used on living subjects. However, even now, the evaluating apparatus needs a considerably complex construction and accordingly has some limits to reduction of production cost.

In this background, the Inventors have performed extensive studies and researches for developing a technique of evaluating arteriosclerosis based on a new index that has never been used. One of the results obtained by the Inventors is such a finding that a relationship between difference of internal and external pressure of artery's wall of each individual subject in a state in which the difference is in equilibrium, and diameter of the artery, or a relationship between the difference of internal and external pressure of artery's wall and amplitude of pulse wave detected from the artery, is specific to the each individual subject. Based on this finding, the Inventors have developed a new arteriosclerosis evaluating apparatus.

SUMMARY OF THE INVENTION

It is therefore an object of the present invention to provide an arteriosclerosis evaluating apparatus which can as easily as possible evaluate arteriosclerosis of a living subject.

The above object has been achieved by the present invention. According to a first aspect of the present invention, there is provided an apparatus for evaluating arteriosclerosis of a living subject, the apparatus comprising an arteriosclerosis evaluating means for evaluating the arteriosclerosis of the subject based on a relationship between difference of internal and external pressure of an artery of the subject in a state in which the difference is in equilibrium, and diameter of the artery.

This arteriosclerosis evaluating apparatus includes the arteriosclerosis evaluating means that evaluates the arteriosclerosis of the subject, based on the relationship between difference of internal and external pressure of the artery of the subject in the state in which the pressure difference is in equilibrium, and diameter of the artery. Therefore, the present apparatus can as easily as possible evaluate the arteriosclerosis of the subject based on the relationship between in-equilibrium pressure difference and artery's diameter that is obtained from, e.g., a pressing pressure of a cuff wound around a certain portion of the subject, and a pulse wave produced from the artery.

According to a second aspect of the present invention, there is provided an apparatus for evaluating arteriosclerosis of a living subject, the apparatus comprising an arteriosclerosis evaluating means for evaluating the arteriosclerosis of the subject based on a relationship between difference of internal and external pressure of an artery of the subject in a state in which the difference is in equilibrium, and amplitude of a pulse wave produced from the artery.

This arteriosclerosis evaluating apparatus includes the arteriosclerosis evaluating means that evaluates the arteriosclerosis of the subject, based on the relationship between in-equilibrium pressure difference and amplitude of pulse wave produced from the artery. Therefore, the present apparatus can as easily as possible evaluate the arteriosclerosis of the subject based on the relationship between in-equilibrium pressure difference and pulse-wave amplitude that is obtained from, e.g., the pressing pressure of the cuff wound around the certain portion of the subject, and the pulse wave produced from the artery.

According to a first feature of the second aspect of the present invention, the arteriosclerosis evaluating means comprises a characteristic curve determining means for determining, as the relationship, a characteristic curve representing respective rates of change, with respect to the difference of internal and external pressure of the artery, of respective amplitudes of a plurality of heartbeat-synchronous pulses of the pulse wave detected from the artery when a pressing pressure externally applied to the artery is changed, and the arteriosclerosis evaluating means evaluates the arteriosclerosis of the subject based on the characteristic curve determined by the characteristic curve determining means. According to this feature, the characteristic curve that reliably reflects the degree of arteriosclerosis of the artery is used as an evaluation index, and accordingly the present apparatus can evaluate the arteriosclerosis of the subject with high reliability.

According to a second feature of the second aspect of the present invention, the arteriosclerosis evaluating means further comprises a regression line determining means for determining a regression line corresponding to the characteristic curve determined by the characteristic curve determining means, and the arteriosclerosis evaluating means evaluates the arteriosclerosis of the subject based on deviation of the characteristic curve from the regression line as a standard line. According to this feature, the deviation of the characteristic curve that reliably reflects the degree of arteriosclerosis of the artery, from the regression line as the standard line, is used as an evaluation index, and accordingly the present apparatus can evaluate the arteriosclerosis of the subject with high reliability.

According to a third feature of the second aspect of the present invention, the arteriosclerosis evaluating means further comprises a rate-of-change calculating means for calculating the respective rates of change, with respect to the difference of internal and external pressure of the artery, of the respective amplitudes of the heartbeat-synchronous pulses of the pulse wave detected from the artery when the pressing pressure externally applied to the artery is changed, and the characteristic curve determining means determines the characteristic curve based on respective straight lines representing the respective rates of change, with respect to the difference of internal and external pressure of the artery, calculated by the rate-of-change calculating means. According to this feature, the present apparatus can as easily as possible determine the characteristic curve and accordingly can evaluate the arteriosclerosis of the subject with high reliability.

According to a fourth feature of the second aspect of the present invention, the difference of internal and external pressure of the artery in the state in which the difference is in equilibrium, is defined as difference of maximum and minimum values, in each of a plurality of heartbeat-synchronous pulses of the pulse wave, of difference of the internal pressure of the artery and a pressing pressure externally applied to the artery. According to this feature, the present apparatus that has, e.g., substantially the same construction as that of a conventional oscillometric blood pressure measuring apparatus, can as easily as possible evaluate the arteriosclerosis of the subject.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Hereinafter, there will be described a preferred embodiment of the present invention in detail by reference to the drawings.

Figure 1:
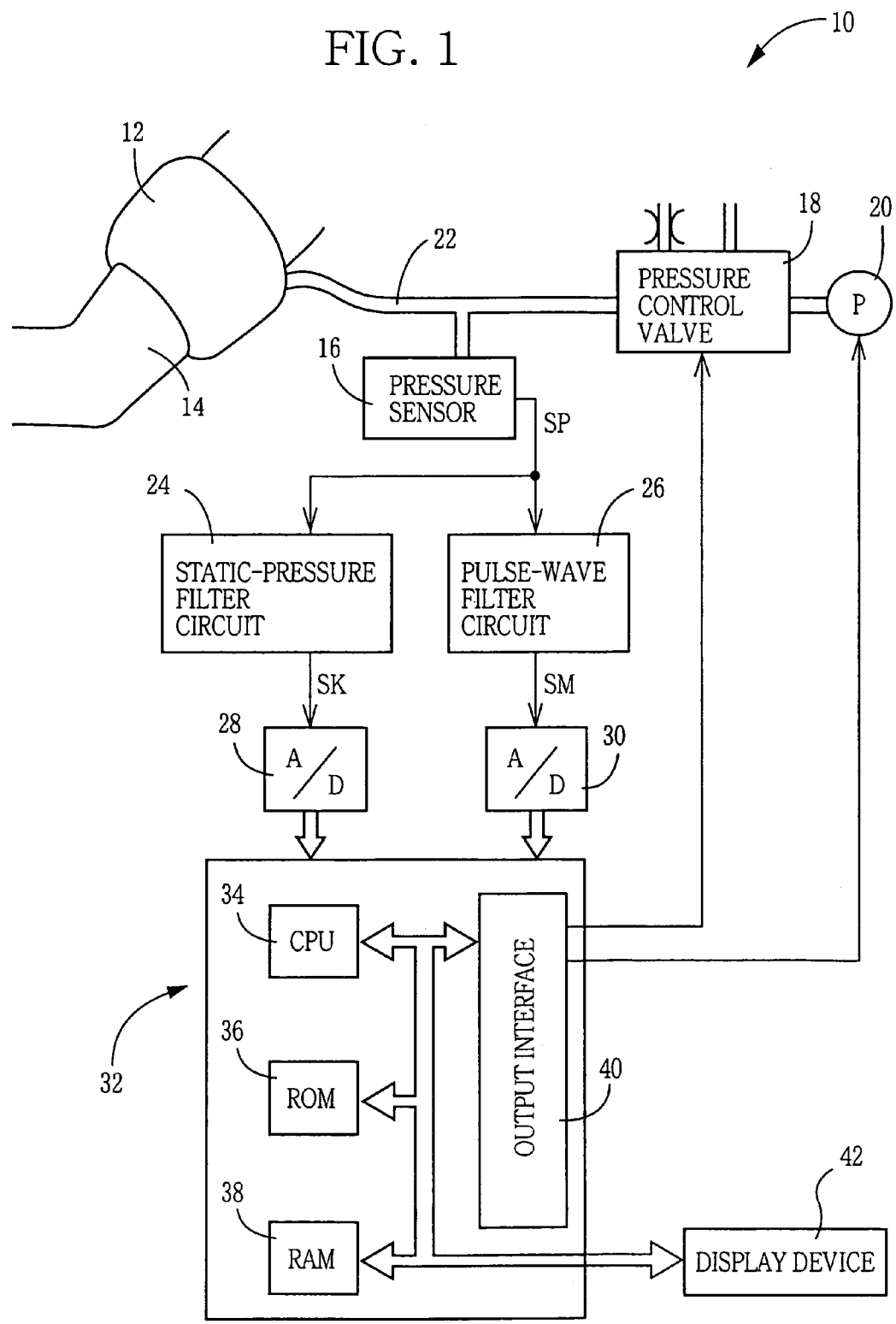
FIG. 1 is a diagrammatic view for explaining a construction of an arteriosclerosis evaluating apparatus to which the present invention is applied.

FIG. 1 is a diagrammatic view for explaining a construction of an arteriosclerosis evaluating apparatus 10 to which the present invention is applied. The arteriosclerosis evaluating apparatus 10 employs an inflatable cuff 12 which includes a belt-like cloth bag and a rubber bag accommodated in the cloth bag and which is adapted to be worn on a brachium 14 of a living subject when arteriosclerosis of the subject is evaluated. The cuff 12 is connected via a piping 22 to a pressure sensor 16, a pressure control valve 18, and an air pump 20. The pressure control valve 18 is switchable to one of three positions, i.e., a pressure supply position in which the control valve 18 allows air pressure (i.e., pressurized air) to be supplied from the air pump 20 to the cuff 12; a slow deflation position in which the control valve 18 slowly deflates the air pressure from the cuff 12; and a quick deflation position in which the control valve 18 quickly deflates the air pressure from the cuff 12.

The pressure sensor 16 detects the air pressure in the cuff 12, and supplies a pressure signal SP representing the detected air pressure, to each of a static-pressure filter circuit 24 and a pulse-wave filter circuit 26. The static-pressure filter circuit 24 includes a low-pass filter which extracts, from the pressure signal SP, a cuff pressure signal SK representing a static component of the detected air pressure, i.e., a pressing pressure Pc of the cuff 12. The filter circuit 24 supplies the cuff pressure signal SK to an electronic control device 32 via an A/D (analog-to-digital) converter 28. The pulse-wave filter circuit 26 includes a band-pass filter which extracts, from the pressure signal SP, a pulse wave signal SM representing an oscillatory component of the detected air pressure that has specific frequencies. The filter circuit 26 supplies the pulse wave signal SM to the electronic control device 32 via an A/D converter 30. The pulse wave signal SM represents a cuff pulse wave Wc that is transmitted from an artery of the brachium 14 to the cuff 12.

The electronic control device 32 is provided by a so-called microcomputer including a CPU (central processing unit) 34, a ROM (read only memory) 36, a RAM (random access memory) 38, and an output interface 40. The CPU 34 processes signals according to control programs pre-stored in the ROM 36, while utilizing a temporary-storage function of the RAM 38. The CPU 34 outputs, from the output interface 40, drive signals to the pressure control valve 18 and the air pump 20 via respective drive circuits (not shown), so as to control the air pressure in the cuff 12. In addition, the CPU 34 processes the cuff pressure signal SK and the pulse wave signal SM supplied to the control device 32 during the control of air pressure in the cuff 12, so as to calculate an arteriosclerosis evaluation value AE of the subject, and operates a display device 42 such as a CRT (cathode ray tube) or LCD (liquid crystal display) to display the thus calculated arteriosclerosis evaluation value AE such that the displayed evaluation value AE can be observed by an observer such as a doctor or a nurse, or the subject himself or herself.

Figure 2:
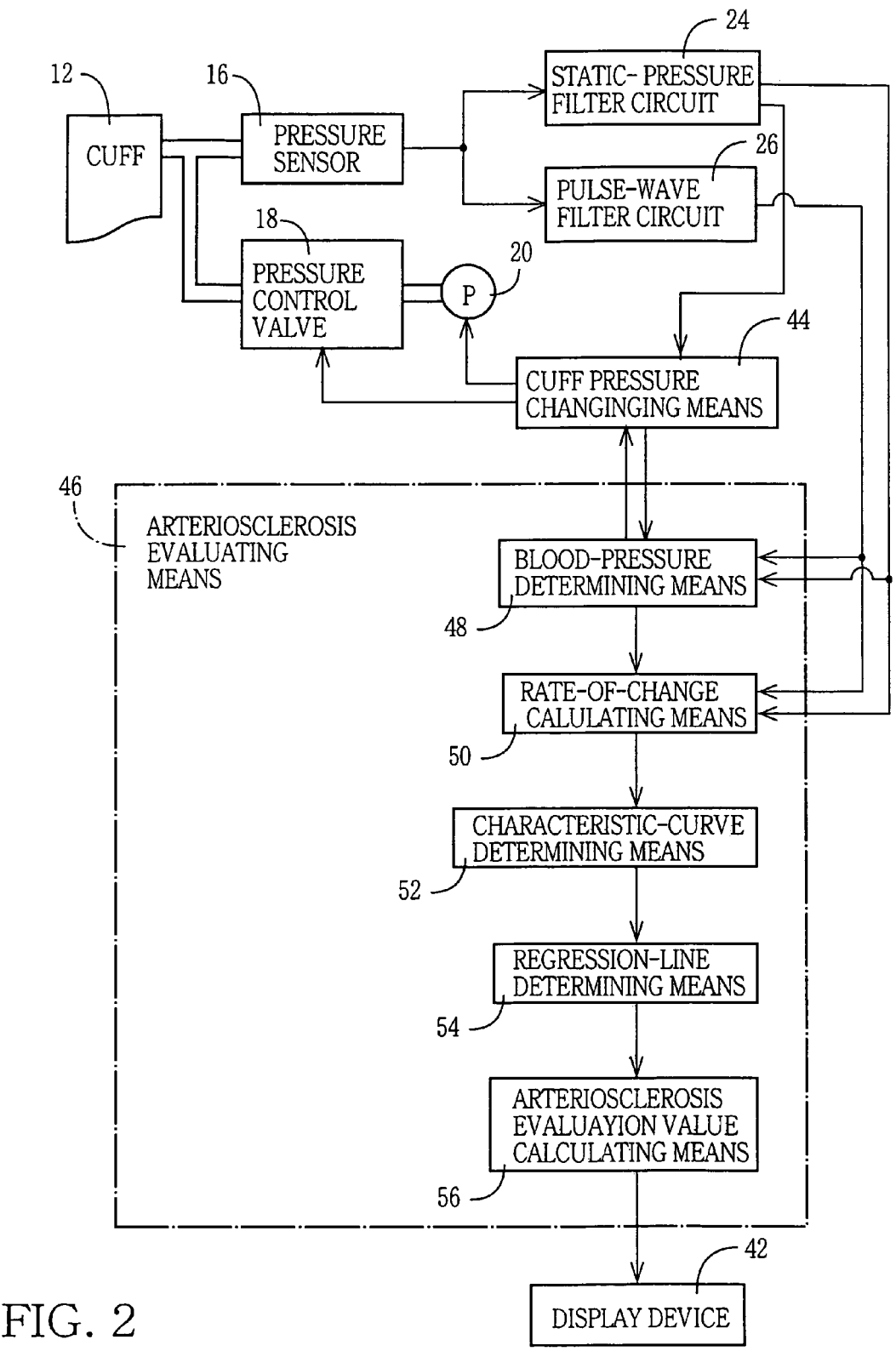
FIG. 2 is a diagrammatic view for explaining essential control functions of an electronic control device of the arteriosclerosis evaluating apparatus of FIG. 1.

FIG. 2 is a diagrammatic view for explaining essential control functions of the electronic control device 32. A cuff-pressure changing device or means 44 reads the pressing pressure Pc of the cuff 12 (hereinafter, referred to as the "cuff pressure Pc") that is represented by the cuff pressure signal SK supplied from the static-pressure filter circuit 24, and controls the pressure control valve 18 and the air pump 20 so as to change the cuff pressure Pc, as follows: First, the cuff pressure Pc is quickly increased up to a prescribed target pressure value Pset (e.g., 180 mmHg) that would be higher than a systolic blood pressure of the brachium 14, and then the cuff pressure Pc is slowly decreased at a rate of about 3 mmHg/sec. After an arteriosclerosis evaluating device or means 46, described later, determines an arteriosclerosis evaluation value AE of the subject, the cuff pressure Pc is quickly decreased to atmospheric pressure.

The arteriosclerosis evaluating device or means 46 includes a blood pressure determining device or means 48, a rate-of-change calculating device or means 50, a characteristic curve determining device or means 52, a regression line determining device or means 54, and an arteriosclerosis evaluation value calculating device or means 56, and evaluates arteriosclerosis of the brachium 14 based on a relationship between difference $\Delta P$ of internal and external pressure of the artery of the brachium 14 in a state in which the pressure difference $\Delta P$ is in equilibrium (hereinafter, referred to as the "in-equilibrium pressure difference $\Delta P$"), and amplitude AM of the pulse wave obtained from the artery, i.e., cuff pulse wave Wc. Meanwhile, the change of pulse-wave amplitude AM can be regarded as the change of diameter $\phi A$ of the artery. Therefore, the arteriosclerosis evaluating device or means 46 can be said as a device or means which evaluates arteriosclerosis of the brachium 14 based on a relationship between in-equilibrium pressure difference $\Delta P$ and change of artery's diameter $\phi A$.

Figure 3:
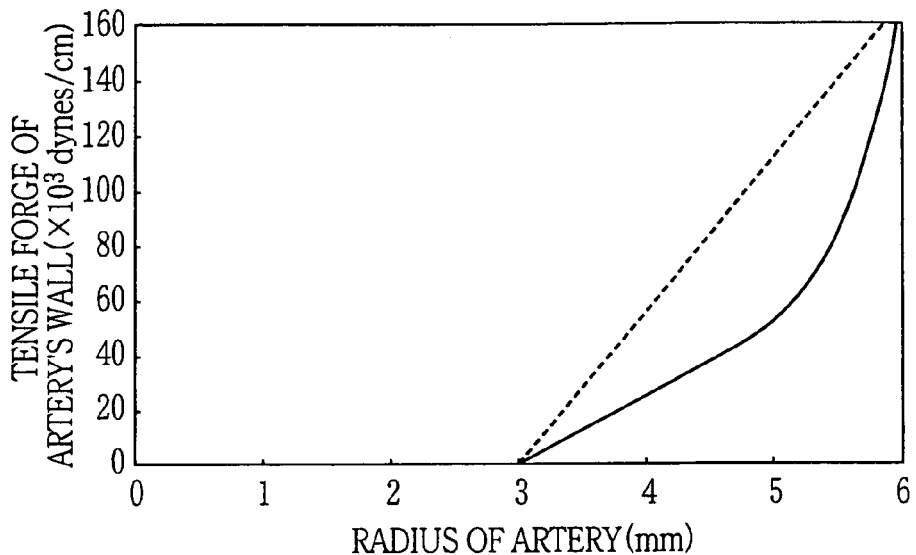
FIG. 3 is a graph showing a curve representing a relationship between artery's radius and tensile force of artery's wall.

FIG. 3 shows a graph representing a relationship between artery's radius and tensile force of artery's wall. If a tube is a linear elastic body (i.e., a Hooke's elastic body), there is a proportional relationship between tube's radius and tensile force of tube's wall, as indicated at broken line. Regarding an artery of a living being, however, a proportional relationship between artery's radius and tensile force of artery's wall weakens as artery's diameter increases, as indicated at solid line. It is said that the reason why the proportional relationship weakens is that the artery's wall is formed of elastic fibers and collagen fibers. Thus, it is also said that a curve representing the relationship between artery's radius and tensile force of artery's wall, indicated at solid line in FIG. 3, is characteristic of the subject's artery and is not influenced by the change of subject's blood pressure and/or pulse rate.

Laplace's law defines another relationship between artery's radius and tensile force of artery's wall. Providing that T is tensile force of artery's wall; $\Delta P$ is difference between internal and external pressure of artery; r is artery's radius; and W is thickness of artery's wall, Laplace's law is expressed by the following equation (1):

$$T=(\Delta P/W) \times r \quad (1)$$

Figure 4:
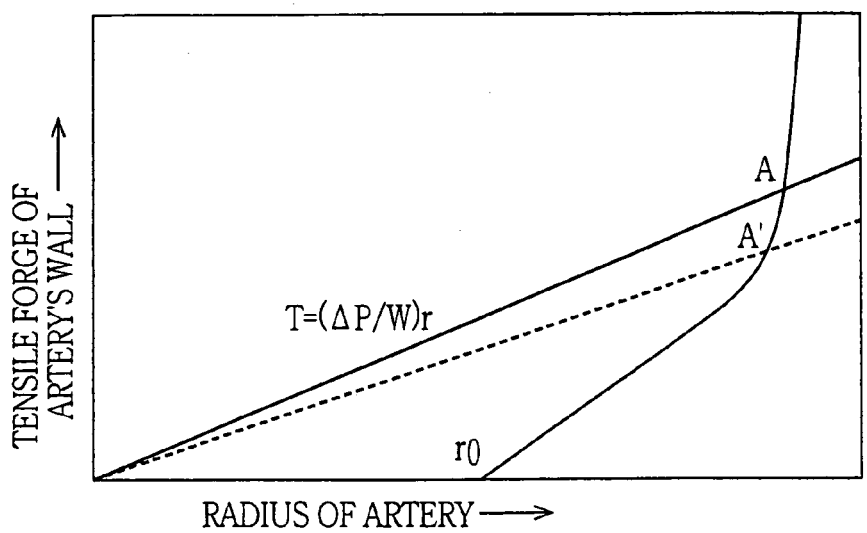
FIG. 4 is a graph showing, in addition to the curve shown in FIG. 3, a straight line representing Laplace's law.

FIG. 4 shows the second relationship defined by Laplace's law, in addition to the first relationship shown in FIG. 3. In FIG. 4, symbol "r0" indicates a radius of the artery when the tensile force of artery's wall is 0 (zero); and symbol "A" indicates a point of intersection of the curve indicated at solid line in FIG. 3 and a straight line representing Laplace's law, that is, the intersection point A indicates a radius of the artery in the state in which the difference $\Delta P$ of internal and external pressure of the artery is in equilibrium. Therefore, when the pressure difference $\Delta P$ changes, the straight line representing Laplace's law also changes as indicated at broken line, and accordingly the intersection point A moves to a new point A'.

It is said that a curve representing a relationship between artery's radius and tensile force of artery's wall, indicated at solid line in FIG. 3, and a thickness W of artery's wall will not change with respect to each individual subject, as far as the relationship and the thickness W are obtained and measured daily or monthly. Thus, it can be speculated that a relationship between in-equilibrium pressure difference $\Delta P$ and artery's diameter $\phi A$, and accordingly a relationship between in-equilibrium pressure difference $\Delta P$ and pulse-wave amplitude AM are specific to each individual subject.

Figure 5:
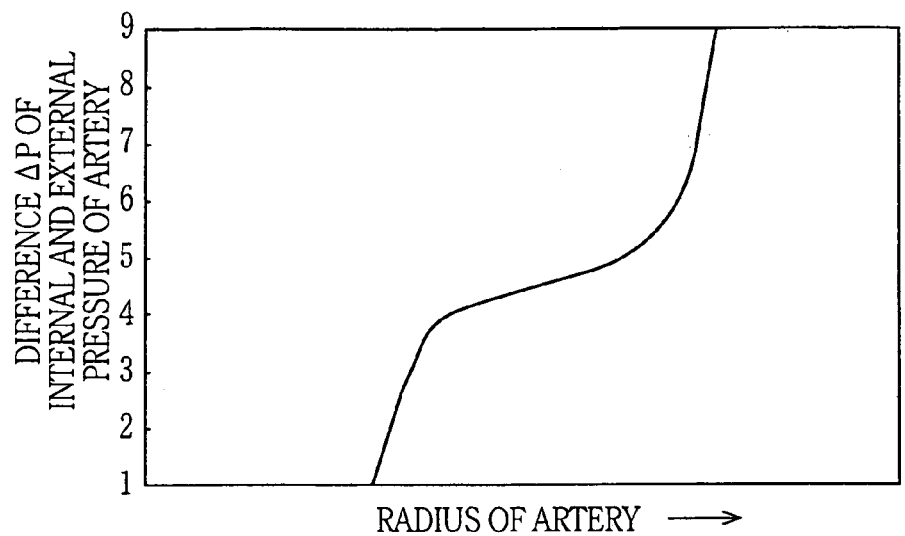
FIG. 5 is a graph showing a curve representing a relationship between difference of internal and external pressure of artery in equilibrium, and artery's diameter.

FIG. 5 shows a graph representing a relationship between in-equilibrium pressure difference $\Delta P$ and artery's diameter $\phi A$. This relationship is specific to each individual subject, and is not influenced by the change of subject's pulse rate and/or blood pressure, or the change of shape of subject's pulse wave caused by arrhythmia.

Preferably, the in-equilibrium pressure difference $\Delta P$ is obtained as a difference between a maximum value PUL and a minimum value PLL, in each heart-synchronous pulse of the pulse wave, of the difference between the internal pressure of the artery and the cuff pressure Pc. Around each of a maximum value and a minimum value of the internal pressure of the artery, i.e., around each of the maximum value PUL and the minimum value PLL, in each heart-synchronous pulse of the pulse wave, of the difference between the internal pressure of the artery and the cuff pressure Pc, the change of internal pressure of the artery stops and accordingly the difference $\Delta P$ of internal and external pressure of the artery is in equilibrium, whereby the in-equilibrium pressure difference ΔP accurately corresponds to the shape (e.g., diameter φA) of the artery. The present arteriosclerosis evaluating apparatus 10 evaluates arteriosclerosis of the subject based on the in-equilibrium pressure difference ΔP defined as indicated above.

Back to FIG. 2, the blood pressure determining means 48 determines the change of the cuff pressure Pc represented by the cuff pressure signal SK supplied from the static-pressure filter circuit 24 during the slow decreasing of the cuff pressure Pc under the control of the cuff pressure changing means 44, and the change of respective amplitudes of successive heartbeat-synchronous pulses of the cuff pulse wave Wc represented by the pulse wave signal SM supplied from the pulse-wave filter circuit 26 during the slow decreasing of the cuff pressure Pc. Then, based on the thus determined changes of the cuff pressure Pc and the respective amplitudes of successive pulses of the cuff pulse wave Wc, the determining means 48 determines a systolic blood pressure $BP_{SYS}$ and a diastolic blood pressure $BP_{DIA}$ of the subject, according to a well-known oscillometric algorithm. In addition, the determining means 48 operates the display device 42 to display the thus determined blood-pressure values BP.

Figure 6:
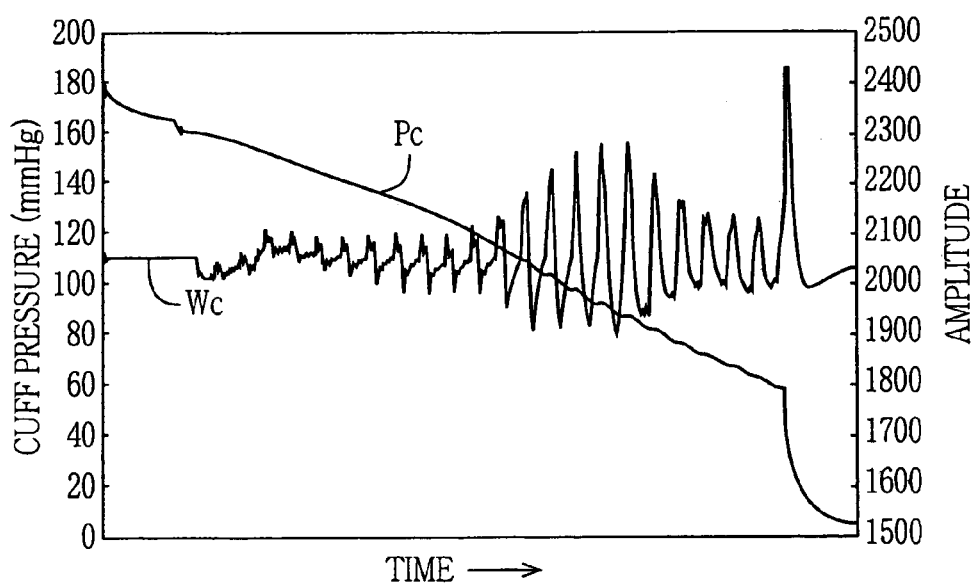
FIG. 6 is a graph showing respective examples of a slow decreasing of a cuff pressure under control of a cuff-pressure changing means shown in FIG. 2, and a cuff pulse wave contained in the cuff pressure.
Figure 7:
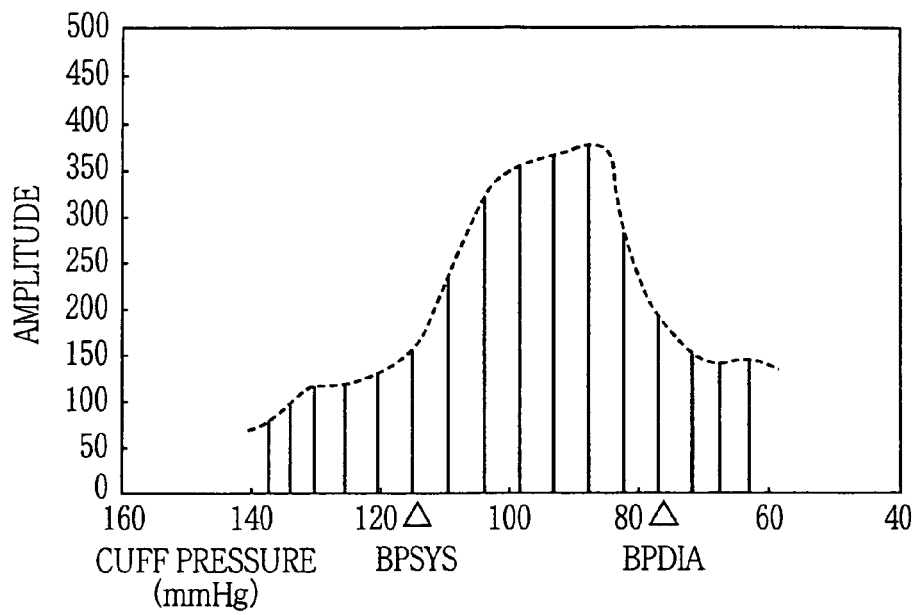
FIG. 7 is a graph showing respective amplitudes of successive heartbeat-synchronous pulses of the cuff pulse wave, shown in FIG. 6, that correspond to respective values of the cuff pressure.

FIG. 6 shows respective examples of the slow decreasing of the cuff pressure Pc under the control of the cuff pressure changing means 44, and the cuff pulse wave Wc contained in that cuff pressure Pc; and FIG. 7 shows the respective amplitudes of successive heartbeat-synchronous pulses of the cuff pulse wave Wc, shown in FIG. 6, that correspond to respective values of the cuff pressure Pc. According to the oscillometric algorithm, the blood-pressure determining means 48 determines a systolic blood pressure $BP_{SYS}$ of 114 mmHg and a diastolic blood pressure $BP_{DIA}$ of 76 mmHg, based on an envelope (indicated at broken line) of the respective amplitudes of successive pulses of the cuff pulse wave Wc that correspond to the respective values of the cuff pressure Pc.

Back to FIG. 2, the rate-of-change calculating means 50 calculates, for each of the successive pulses of the cuff pulse wave Wc detected from the artery during the slow decreasing of the cuff pressure Pc under the control of the cuff pressure changing means 44, a rate of change of the amplitude AM of the each pulse with respect to the in-equilibrium pressure difference ΔP defined as described above. The thus calculated respective rates of change for the successive pulses of the cuff pulse wave Wc reflect the change of artery's diameter φA corresponding to the change of pulse amplitude AM, and are used to provide a characteristic curve 58 (FIG. 11), described later.

Figure 8:
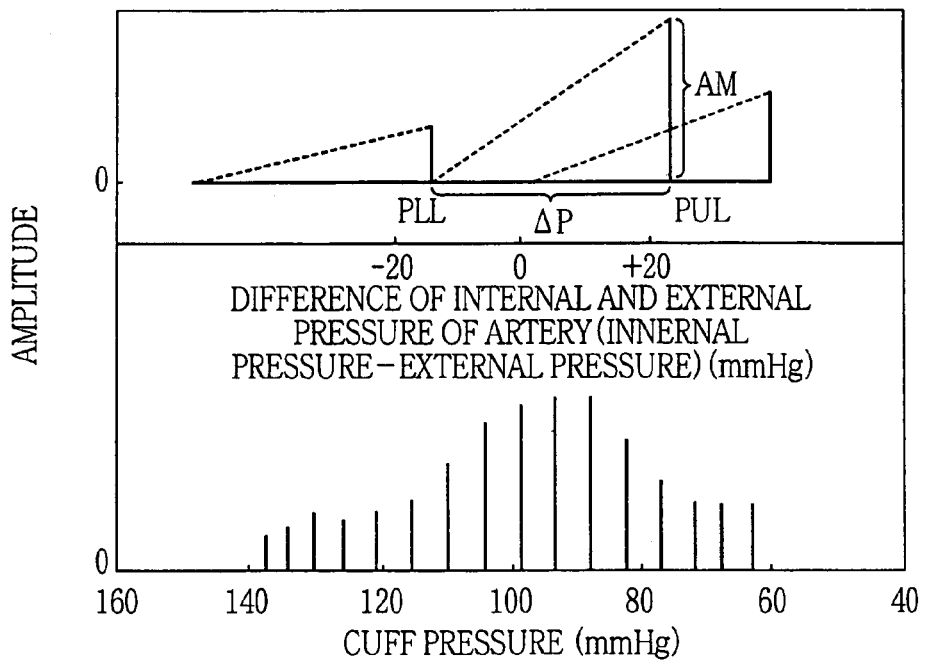
FIG. 8 is a graph for explaining a method of calculating, for each of the successive heartbeat-synchronous pulses of the cuff pulse wave, a rate of change of the amplitude of the each pulse with respect to the in-equilibrium pressure difference, i.e., the difference of maximum and minimum values, in the each pulse, of the difference between the internal pressure of an artery and the cuff pressure.
Figure 9:
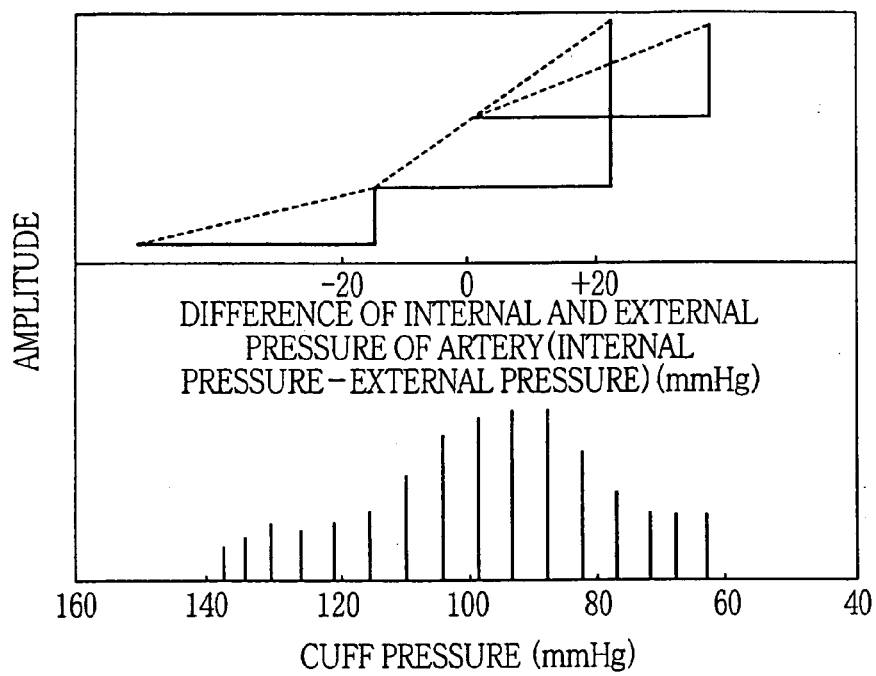
FIG. 9 is another graph for explaining the method of calculating the rate of change of the amplitude of the each pulse with respect to the in-equilibrium pressure difference.
Figure 10:
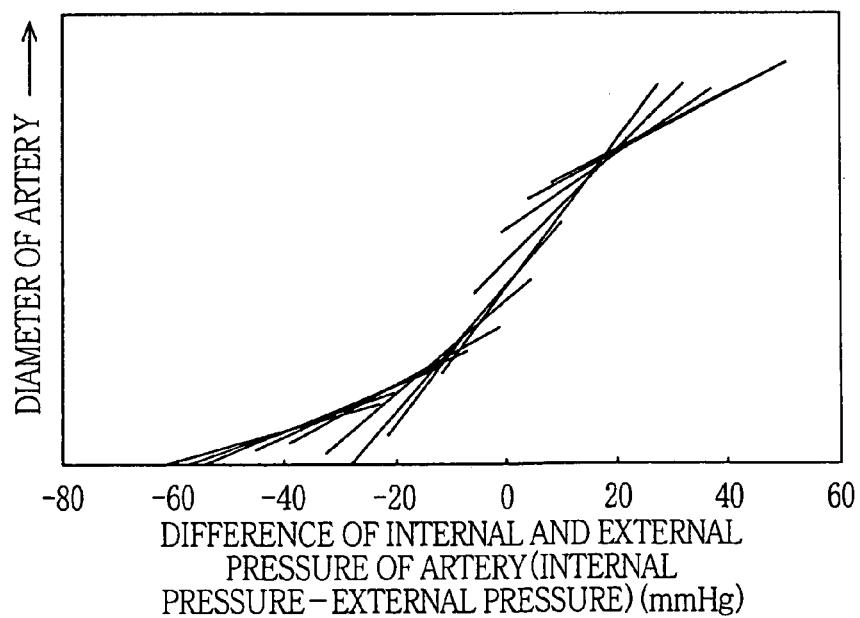
FIG. 10 is yet another graph for explaining the method of calculating the rate of change of the amplitude of the each pulse with respect to the in-equilibrium pressure difference.

FIGS. 8, 9, and 10 show graphs for explaining a manner in which the rate-of-change calculating means 50 calculates the rate of change of the amplitude AM of each pulse with respect to the in-equilibrium pressure difference ΔP. FIG. 8 shows three exemplary values, 75 mmHg, 98 mmHg, 130 mmHg, of the cuff pressure Pc for each of which the calculating means 50 calculates a rate of change of amplitude AM of each pulse with respect to an in-equilibrium pressure difference ΔP that is equal to the difference of maximum and minimum values PUL, PLL, in the each pulse, of the difference of the internal pressure of the artery and the cuff pressure Pc. The thus calculated rate of change is indicated by a slope of a broken line shown in the figure. This rate of change means an average rate of change of amplitude AM of the cuff pulse wave Wc in an interval of the cuff pressure Pc between (cuff pressure Pc–systolic blood pressure $BP_{SYS}$) and (cuff pressure Pc–diastolic blood pressure $BP_{DIA}$).

Back to FIG. 2, the characteristic curve determining means 52 first determines respective straight lines representing the respective rates of change, calculated by the rate-of-change calculating means 50, of the respective amplitudes AM of successive pulses of the cuff pulse wave Wc detected from the artery during the changing of the cuff pressure Pc, and then determines, as the above-described relationship between in-equilibrium pressure difference ΔP and amplitude AM of the cuff pulse wave Wc, a characteristic curve 58 representing the respective rates of change of the respective amplitudes AM of successive pulses of the cuff pulse wave Wc with respect to the in-equilibrium pressure difference ΔP, based on the thus determined straight lines.

Figure 11:
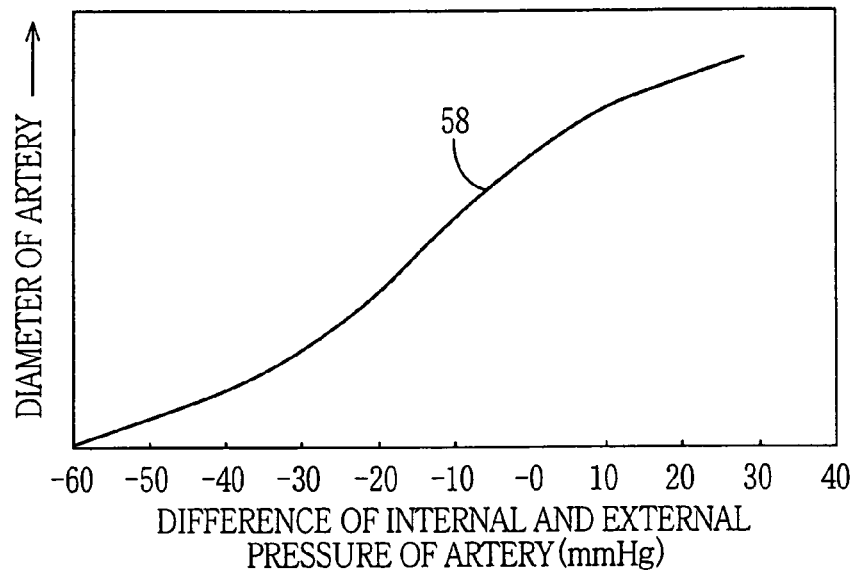
FIG. 11 is a graph showing a characteristic curve representing the respective rates of change of the respective amplitudes of successive pulses of the cuff pulse wave shown in FIG. 6.

As explained above, it can be speculated that the relationship between in-equilibrium pressure difference ΔP and pulse-wave amplitude AM is specific to each individual subject. Therefore, as shown in FIG. 9, the respective amplitudes AM of successive pulses of the cuff pulse wave Wc, shown in FIG. 8, should be connected to each other on an axis of ordinates indicative of pulse-wave amplitude. FIG. 10 shows that the respective straight lines representing the respective rates of change of the respective amplitudes AM of successive pulses of the cuff pulse wave Wc detected from the artery during the changing of the cuff pressure Pc, that is, the broken lines shown in FIG. 9 are connected to each other. The characteristic curve 58 shown in FIG. 11 is obtained by connecting respective points of intersection of the straight lines, shown in FIG. 10, to each other.

Figure 12:
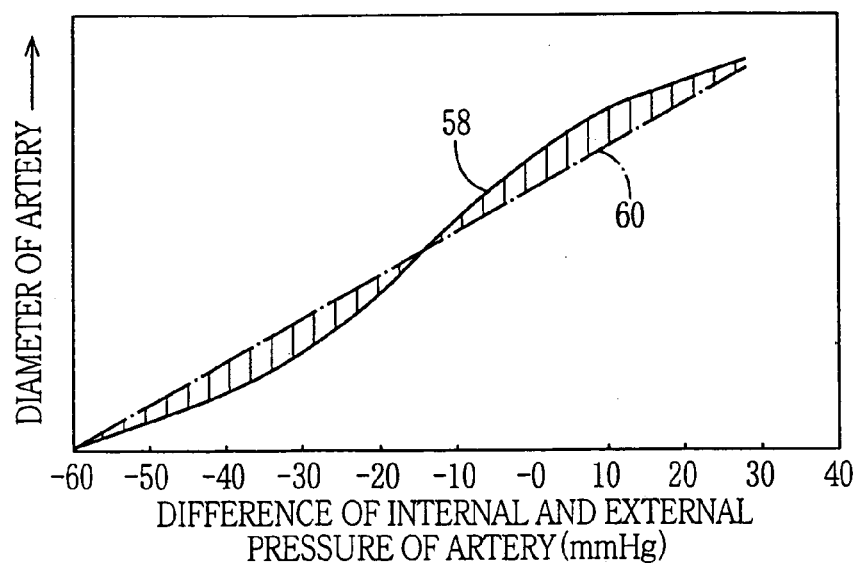
FIG. 12 is a graph showing a regression line corresponding to the characteristic curve shown in FIG. 11.

Back to FIG. 2, the regression line determining means 54 determines a regression line 60 corresponding to the characteristic curve 58 determined by the characteristic curve determining means 52. FIG. 12 shows the characteristic curve 58, and the regression line 60 corresponding to the characteristic curve 58, so that the curves and lines 58, 60 can be compared with each other. The regression line 60 is a straight line that is determined by well-known least square method.

In FIG. 2, the arteriosclerosis evaluation value calculating means 56 calculates, as an arteriosclerosis evaluation value AE of the subject, an amount of deviation of the characteristic curve 58 from the regression line 60 as a standard line that is determined by the regression line determining means 54, and operates the display device 42 to display the thus determined arteriosclerosis evaluation value AE.

Figure 13:
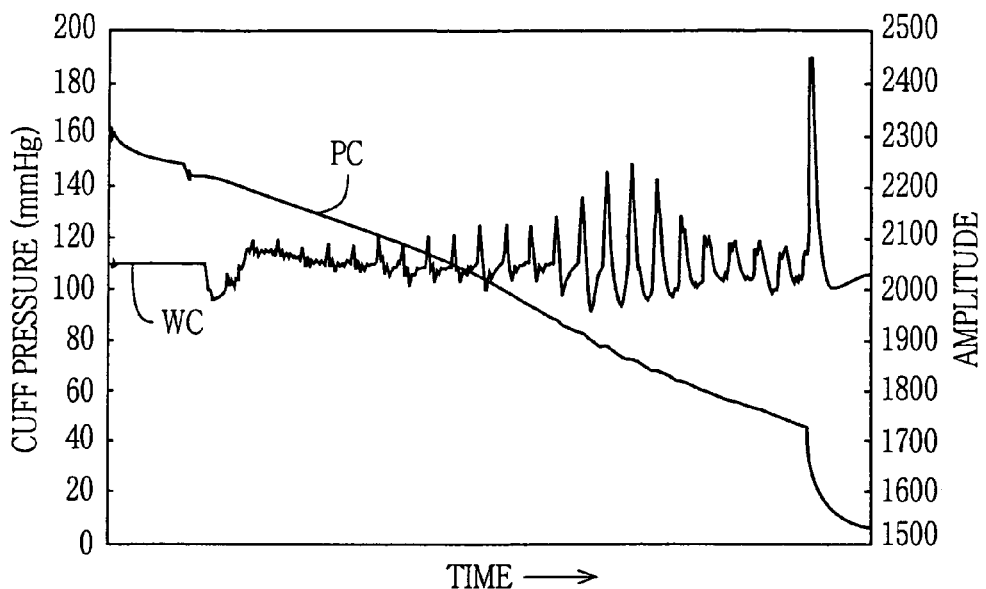
FIG. 13 is a graph corresponding to FIG. 6, showing a slow decreasing of a cuff pressure, and a cuff pulse wave that was contained in the cuff pressure and was obtained from a living subject, who gave the results shown in FIG. 6, when the subject exhibited different systolic blood pressure and pulse-wave amplitude than those the subject exhibited when having given the results shown in FIG. 6.

FIG. 13 shows a slow decreasing of the cuff pressure Pc and a cuff pulse wave Wc contained in the cuff pressure Pc that were obtained from the subject who gave the results shown in FIG. 6 but whose systolic blood pressure $BP_{SYS}$ and pulse-wave amplitude AM decreased by 88 mmHg and 40%, respectively. From the results shown in FIG. 13, the blood pressure determining means 48, the rate-of-change calculating means 50, and the characteristic curve determining means 52 cooperate with each other to determine a characteristic curve 62, indicated at broken line in FIG. 14. From comparison of the two characteristic curves 58, 62 with each other, it can be understood that the two curves 58, 62 somewhat differ from each other in a high, positive range of the difference ΔP of internal and external pressure of the artery, but generally resemble each other. This means that a relationship between in-equilibrium pressure difference ΔP and artery's diameter φA, or a relationship between in-equilibrium pressure difference ΔP and pulse-wave amplitude AM is specific to each individual subject.

Figure 14:
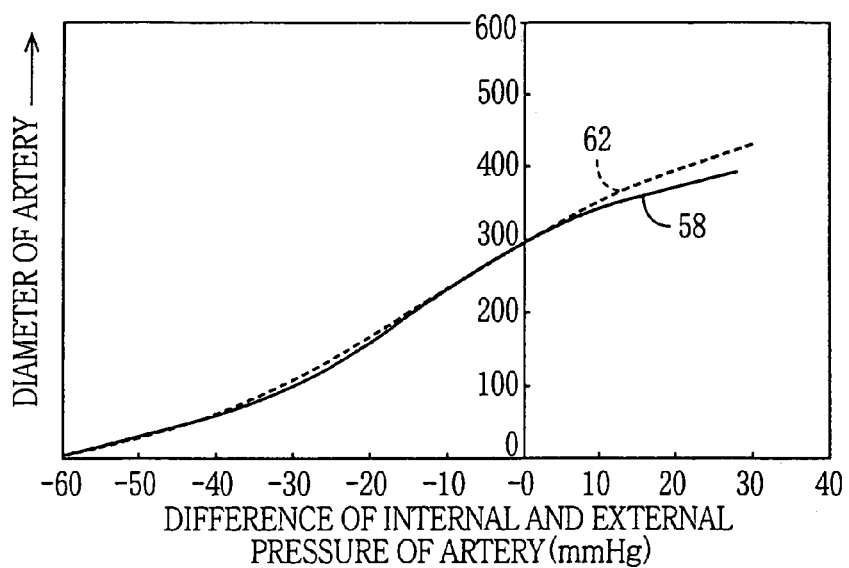
FIG. 14 is a graph showing, in addition to the characteristic curve shown in FIG. 11, a characteristic curve representing respective rates of change of respective amplitudes of successive pulses of the cuff pulse wave shown in FIG. 13.
Figure 15:
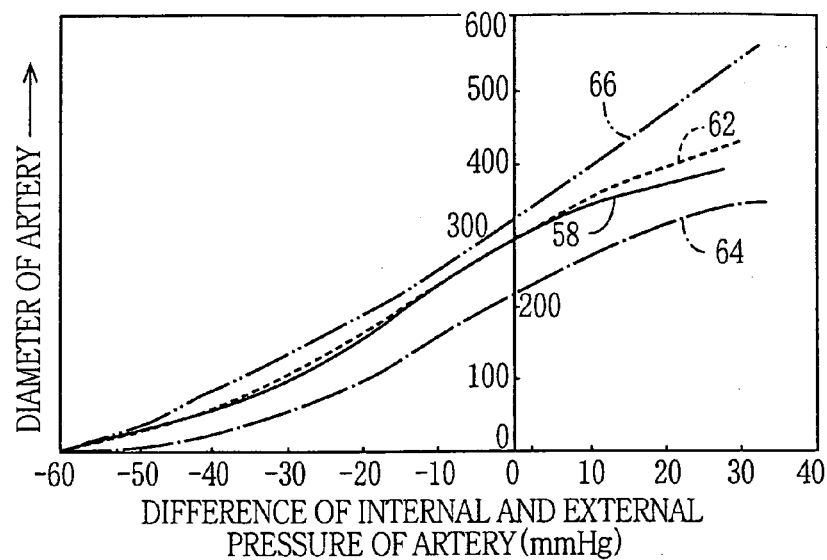
FIG. 15 is a graph showing, in addition to the characteristic curves shown in FIG. 14, respective characteristic curves obtained from respective arteries of two living subjects different from the subject who gave the characteristic curves shown in FIG. 14.

FIG. 15 shows respective characteristic curves that were obtained from respective arteries of two living subjects different from the first subject who gave the characteristic curves shown in FIG. 14. In FIG. 15, a second characteristic curve 64, indicated at one-dot chain line, was obtained from an artery of the second subject whose degree of arteriosclerosis is considerably low; and a characteristic curve 66, indicated at two-dot chain line, was obtained from an artery of the third subject whose degree of arteriosclerosis is considerably high. From comparison of the first characteristic curve 58 with the second and third characteristic curves 64, 66, it can be understood that the first characteristic curve 58 has a shape significantly different from those of the second and third characteristic curves 64, 66. This also means that a relationship between in-equilibrium pressure difference $\Delta P$ and artery's diameter $\phi A$, or a relationship between in-equilibrium pressure difference $\Delta P$ and pulse-wave amplitude AM is specific to each individual subject.

In FIG. 15, the shape of characteristic curve 66 obtained from the artery of the third subject whose degree of arteriosclerosis is considerably high, is nearer to a straight line than those of characteristic curves 58, 62, 64 obtained from the respective arteries of the first and second subjects whose degrees of arteriosclerosis are considerably low. Thus, as degree of arteriosclerosis increases, the shape of characteristic curve approaches regression line, and accordingly the amount of deviation of the characteristic curve from the regression line decreases. Conversely, as degree of arteriosclerosis decreases, the shape of characteristic curve deviates from regression line, and accordingly the amount of deviation of the characteristic curve from the regression line increases. Back to FIG. 12, the sum of respective amounts of deviation of the characteristic curve 58 from the regression line 60 as the standard line corresponds to an area enclosed by the characteristic curve 58 and the regression line 60. Therefore, the arteriosclerosis evaluation value AE can be defined as a parameter that is in inverse proportion to the area and thus it can be easily expressed in terms of figures.

Figure 16:
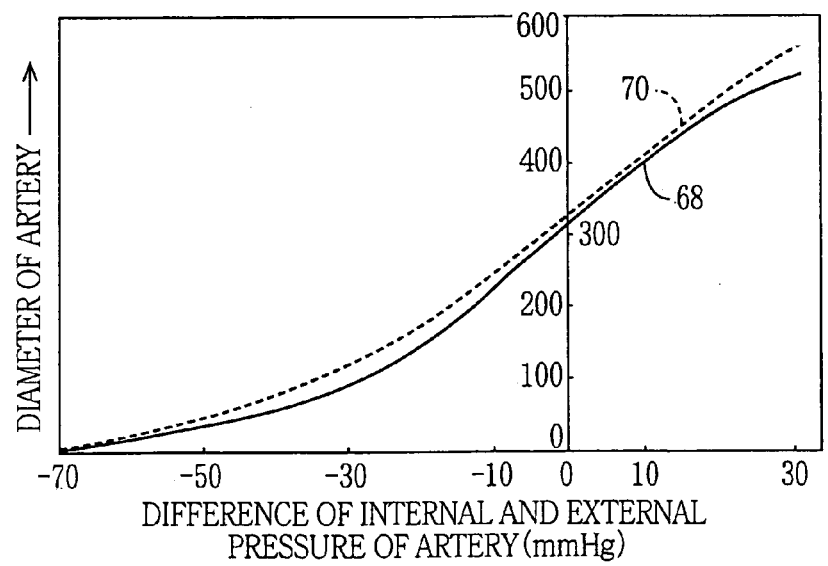
FIG. 16 is a graph showing respective characteristic curves obtained from an artery of a living subject different from the three subjects who gave the characteristic curves shown in FIG. 15.

FIG. 16 shows two characteristic curves obtained from an artery of a fourth subject. A characteristic curve 68, indicated at solid line, and a characteristic curve 70, indicated at broken line, were each obtained from the fourth subject, when the fourth subject exhibited different systolic blood pressure values $BP_{SYS}$ and different pulse-wave amplitudes AM. From comparison of the two characteristic curves 68, 70 with each other, it can be understood that the two curves 68, 70 substantially resemble with each other in shape. This result also supports the above-indicated speculation that a characteristic curve determined according to the present invention is specific or proper to each individual subject.

Figure 17:
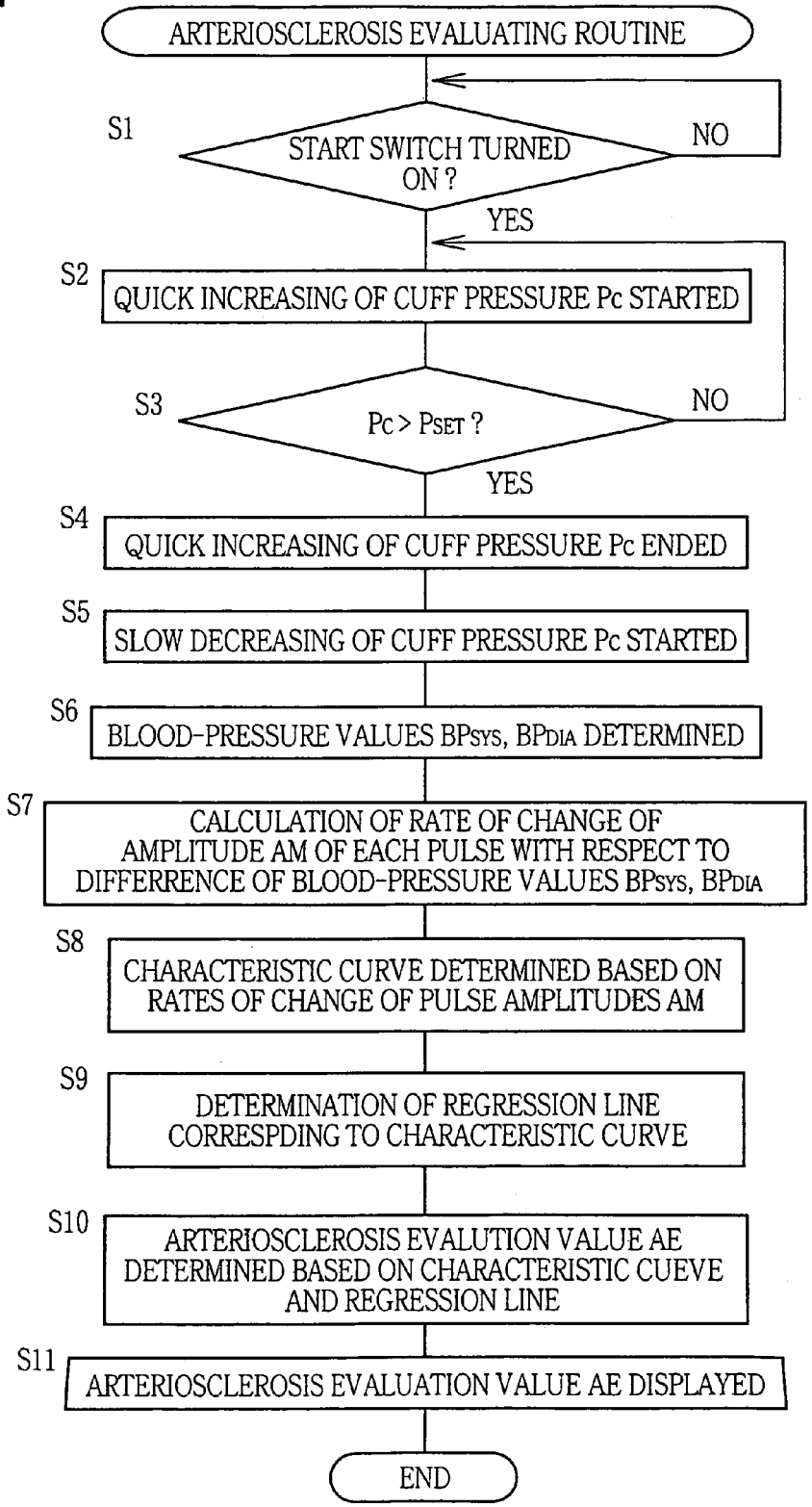
FIG. 17 is a flow chart representing an arteriosclerosis evaluation control of the electronic control device shown in FIG. 2.

FIG. 17 shows a flow chart for explaining the essential control functions of the control device 32, shown in the diagrammatic view of FIG. 2, that are for evaluating arteriosclerosis of a living subject. According to this flow chart, first, at Step S1, the control device judges whether a start switch, not shown, has been operated. While a negative judgment is made at Step S1, the control device repeats Step S1. Meanwhile, if a positive judgment is made at Step S1, the control goes to Step S2 where the control device operates the air pump 20, and switches the pressure control valve 18 to its pressure supply position, so as to increase quickly the pressing pressure Pc of the cuff 12, at a prescribed high rate.

Subsequently, at Step S3, the control device judges whether the cuff pressure Pc is greater than a prescribed target pressure value Pset. While a negative judgment is made at Step S3, the control device repeats Steps S2 and S3 to continue quickly increasing the cuff pressure Pc. Meanwhile, if a positive judgment is made at Step S3, the control goes to Step S4 to stop the air pump 20 and thereby stop increasing the cuff pressure Pc.

Next, at Step S5, the control device switches the pressure control valve 18 to its slow deflation position so as to decrease slowly the cuff pressure Pc at a prescribed low rate. Then, the control goes to Step S6 corresponding to the blood-pressure determining means 48. That is, the control device determines respective amplitudes AM of successive heartbeat-synchronous pulses of the cuff pulse wave Wc represented by the pulse-wave signal SM continuously supplied from the pulse-wave filter circuit 26, and respective values of the cuff pressure Pc represented by the cuff pressure signal SK continuously supplied from the static-pressure filter circuit 24, at respective times of detection of the successive pulses of the cuff pulse wave Wc. Based on the change of the pulse amplitudes AM and the respective values of the cuff pressure Pc, the control device determines a systolic blood pressure $BP_{SYS}$ and a diastolic blood pressure $BP_{DIA}$ of the subject according to a well-known oscillometric blood-pressure determining algorithm.

Subsequently, at Step S7 corresponding to the rate-of-change calculating means 50, the control device calculates, for each of the successive heartbeat-synchronous pulses of the cuff pulse wave Wc detected from the artery during the slow decreasing of the cuff pressure Pc, a rate of change of the amplitude AM of the each pulse with respect to the in-equilibrium pressure difference $\Delta P$, i.e., the difference of maximum and minimum values PUL, PLL, in the each pulse, of the difference between the internal pressure of the artery and the cuff pressure Pc.

Subsequently, at Step S8 corresponding to the characteristic-curve determining means 52, the control device first determines respective straight lines representing the respective rates of change, calculated at Step S7, of the respective amplitudes AM of successive pulses of the cuff pulse wave Wc detected from the artery during the changing of the cuff pressure Pc, and then determines a characteristic curve 58 representing the respective rates of change of the respective amplitudes AM with respect to the in-equilibrium pressure difference $\Delta P$, based on the thus determined straight lines.

Subsequently, at Step S9 corresponding to the regression-line determining means 54, the control device determines, by well-known least square method, a regression line 60 corresponding to the characteristic curve 58 determined at Step S8.

Next, at Step S10 corresponding to the arteriosclerosis evaluation value calculating means 56, the control device calculates, as an arteriosclerosis evaluation value AE of the subject, an amount of deviation of the characteristic curve 58 determined at Step S8, from the regression line 60 as a standard line, determined at Step S9.

Finally, at Step S11, the control device operates the display device 42 to display the arteriosclerosis evaluation value AE determined at Step S10. Thus, the present routine is finished. In the present embodiment, Steps S7, S8, S9, and S10 correspond to the arteriosclerosis evaluating means 46.

It emerges from the foregoing description that the arteriosclerosis evaluating apparatus 10 employs the arteriosclerosis evaluating means 46 (Steps S7, S8, S9, and S10) that evaluates the arteriosclerosis of the subject, based on the relationship between difference $\Delta P$ of internal and external pressure of the artery of the subject in the state in which the pressure difference $\Delta P$ is in equilibrium, and diameter $\phi A$ of the artery. Therefore, the present apparatus 10 can as easily as possible evaluate the arteriosclerosis of the subject based on the relationship between in-equilibrium pressure difference ΔP and artery's diameter φA that is obtained from the pressing pressure Pc of the cuff 12 wound around the brachium 14 of the subject, and the pulse wave Wc produced from the artery.

In addition, the arteriosclerosis evaluating apparatus 10 employs the arteriosclerosis evaluating means 46 that evaluates the arteriosclerosis of the subject, based on the relationship between in-equilibrium pressure difference ΔP and amplitude AM of pulse wave Wc produced from the artery. Therefore, the present apparatus 10 can as easily as possible evaluate the arteriosclerosis of the subject based on the relationship between in-equilibrium pressure difference ΔP and pulse-wave amplitude AM that is obtained from the pressing pressure Pc of the cuff 12 wound around the brachium 14 of the subject, and the pulse wave Wc produced from the artery.

The arteriosclerosis evaluating means 46 includes the characteristic curve determining means 52 (Step S8) that determines, as the above-described relationship, the characteristic curve 58 representing the respective rates of change of the respective amplitudes AM of successive pulses of the pulse wave Wc with respect to the in-equilibrium pressure difference ΔP. The pulse wave Wc is detected from the artery during the changing of the cuff pressure Pc. The thus determined characteristic curve 58 is used to evaluate the arteriosclerosis of the subject. Since the characteristic curve 58 that reliably reflects the degree of arteriosclerosis of the artery is used as an index, the present apparatus 10 can evaluate the arteriosclerosis of the subject with high reliability.

The arteriosclerosis evaluating means 46 includes the regression line determining means 54 (Step S9) that determines the regression line 60 corresponding to the characteristic curve 58 determined by the characteristic curve determining means 52. The deviation of the characteristic curve 58 from the regression line 60 as the standard line is used to evaluate the arteriosclerosis of the subject. Since the deviation of the characteristic curve 58 that reliably reflects the degree of arteriosclerosis of the artery, from the regression line 60 as the standard line, is used as an index, the present apparatus 10 can evaluate the arteriosclerosis of the subject with high reliability.

The arteriosclerosis evaluating means 46 includes the rate-of-change calculating means 50 (Step S7) that calculates, for each of the successive pulses of the pulse wave Wc detected from the artery during the changing of the cuff pressure Pc, the rate of change of the amplitude AM of the each pulse with respect to the in-equilibrium pressure difference ΔP. The characteristic curve determining means 52 first determines the respective straight lines representing the respective rates of change, calculated by the rate-of-change calculating means 50, of the respective amplitudes AM of successive pulses of the pulse wave Wc with respect to the in-equilibrium pressure difference ΔP, and then determines, based on those straight lines, the characteristic curve 58. Thus, the present apparatus 10 can as easily as possible determine the characteristic curve 58 and accordingly can evaluate the arteriosclerosis of the subject with high reliability.

In the illustrated embodiment, the in-equilibrium pressure difference ΔP, i.e., the difference ΔP of internal and external pressure of the artery of the subject in the state in which the pressure difference ΔP is in equilibrium, is defined as the difference of maximum and minimum values PUL, PLL of the difference of the artery's internal pressure and the cuff pressure Pc in each of the respective heartbeat-synchronous pulses of the pulse wave Wc. Therefore, the present apparatus 10 that has substantially the same construction as that of a conventional oscillometric blood pressure measuring apparatus, can as easily as possible evaluate the arteriosclerosis of the subject.

While the present invention has been described in detail in its embodiment by reference to the drawings, it is to be understood that the invention may otherwise be embodied.

For example, the above-described arteriosclerosis evaluating apparatus 10 evaluates the arteriosclerosis of the subject based on the deviation of the characteristic curve 58 from the regression line 60 as the standard line. However, the present invention is by no means limited to this feature. For example, it is possible to evaluate the arteriosclerosis of the subject based on the graphical representation of the above-described relationship, i.e., the characteristic curve 58. In the latter case, the display device 42 displays the characteristic curve 58 itself.

The characteristic curve 58 is just an example of the relationship between in-equilibrium pressure difference ΔP and pulse-wave amplitude AM. Therefore, it is possible to evaluate the arteriosclerosis of the subject based on a different index.

The in-equilibrium pressure difference ΔP is defined as the difference of maximum and minimum values PUL, PLL of the difference of the artery's internal pressure and the cuff pressure Pc in each of the respective heartbeat-synchronous pulses of the pulse wave Wc. This is also just a preferred example of the in-equilibrium pressure difference ΔP. Thus, it is possible to evaluate the arteriosclerosis of the subject by using an in-equilibrium pressure difference ΔP having a different definition.

It is to be understood that the present invention may be embodied with other changes, improvements and modifications that may occur to a person skilled in the art without departing from the spirit and scope of the invention defined in the appended claims.

What is claimed is:

1. An apparatus for evaluating arteriosclerosis of a living subject, the apparatus comprising:
   an arteriosclerosis evaluating means for evaluating the arteriosclerosis of the subject based on a relationship between difference of internal and external pressure of an artery of the subject in a state in which said difference is in equilibrium, and diameter of the artery.

2. An apparatus for evaluating arteriosclerosis of a living subject, the apparatus comprising:
   an arteriosclerosis evaluating means for evaluating the arteriosclerosis of the subject based on a relationship between difference of internal and external pressure of an artery of the subject in a state in which said difference is in equilibrium, and amplitude of a pulse wave produced from the artery.

3. The apparatus according to claim 2, wherein the arteriosclerosis evaluating means comprises a characteristic curve determining means for determining, as said relationship, a characteristic curve representing respective rates of change, with respect to said difference of internal and external pressure of the artery, of respective amplitudes of a plurality of heartbeat-synchronous pulses of the pulse wave detected from the artery when a pressing pressure externally applied to the artery is changed, and wherein the arteriosclerosis evaluating means evaluates the arteriosclerosis of the subject based on the characteristic curve determined by the characteristic curve determining means.

4. The apparatus according to claim 3, wherein the arteriosclerosis evaluating means further comprises a regression line determining means for determining a regression line corresponding to the characteristic curve determined by the characteristic curve determining means, and wherein the arteriosclerosis evaluating means evaluates the arteriosclerosis of the subject based on deviation of the characteristic curve from the regression line as a standard line.

5. The apparatus according to claim 3, wherein the arteriosclerosis evaluating means further comprises a rate-of-change calculating means for calculating the respective rates of change, with respect to said difference of internal and external pressure of the artery, of the respective amplitudes of the heartbeat-synchronous pulses of the pulse wave detected from the artery when the pressing pressure externally applied to the artery is changed, and wherein the characteristic curve determining means determines the characteristic curve based on respective straight lines representing said respective rates of change, with respect to said difference of internal and external pressure of the artery, calculated by the rate-of-change calculating means.

6. The apparatus according to claim 3, wherein said difference of internal and external pressure of the artery in the state in which said difference is in equilibrium, is defined as difference of maximum and minimum values, in each of a plurality of heartbeat-synchronous pulses of the pulse wave, of difference of the internal pressure of the artery and a pressing pressure externally applied to the artery.

7. An apparatus for evaluating arteriosclerosis of a living subject, the apparatus comprising:
an arteriosclerosis evaluating device which evaluates the arteriosclerosis of the subject based on a relationship between difference of internal and external pressure of an artery of the subject in a state in which said difference is in equilibrium, and diameter of the artery.

8. The apparatus according to claim 7, further comprising a relationship obtaining device which obtains said relationship.

9. An apparatus for evaluating arteriosclerosis of a living subject, the apparatus comprising:
an arteriosclerosis evaluating device which evaluates the arteriosclerosis of the subject based on a relationship between difference of internal and external pressure of an artery of the subject in a state in which said difference is in equilibrium, and amplitude of a pulse wave produced from the artery.

10. The apparatus according to claim 9, further comprising a relationship obtaining device which obtains said relationship.

11. The apparatus according to claim 9, wherein the arteriosclerosis evaluating device comprises a characteristic curve determining device which determines, as said relationship, a characteristic curve representing respective rates of change, with respect to said difference of internal and external pressure of the artery, of respective amplitudes of a plurality of heartbeat-synchronous pulses of the pulse wave detected from the artery when a pressing pressure externally applied to the artery is changed, and wherein the arteriosclerosis evaluating means evaluates the arteriosclerosis of the subject based on the characteristic curve determined by the characteristic curve determining means.

12. The apparatus according to claim 11, wherein the arteriosclerosis evaluating device further comprises a regression line determining device which determines a regression line corresponding to the characteristic curve determined by the characteristic curve determining means, and wherein the arteriosclerosis evaluating means evaluates the arteriosclerosis of the subject based on deviation of the characteristic curve from the regression line as a standard line.

13. The apparatus according to claim 11, wherein the arteriosclerosis evaluating device further comprises a rate-of-change calculating device which calculates the respective rates of change, with respect to said difference of internal and external pressure of the artery, of the respective amplitudes of the heartbeat-synchronous pulses of the pulse wave detected from the artery when the pressing pressure externally applied to the artery is changed, and wherein the characteristic curve determining means determines the characteristic curve based on respective straight lines representing said respective rates of change, with respect to said difference of internal and external pressure of the artery, calculated by the rate-of-change calculating means.

* * * * *